(12) United States Patent
Kitano et al.

(10) Patent No.: US 11,608,447 B2
(45) Date of Patent: Mar. 21, 2023

(54) MATERIAL FOR CELL PATTERNING USE

(71) Applicants: THE UNIVERSITY OF TOYAMA, Toyama (JP); OSAKA ORGANIC CHEMICAL INDUSTRY CO., LTD., Osaka (JP)

(72) Inventors: Hiromi Kitano, Toyama (JP); Tadashi Nakaji, Toyama (JP); Yoshiyuki Saruwatari, Osaka (JP); Kazuyoshi Matsuoka, Osaka (JP)

(73) Assignees: THE UNIVERSITY OF TOYAMA, Toyama (JP); OSAKA ORGANIC CHEMICAL INDUSTRY CO., LTD., Osaka (JP)

( * ) Notice: Subject to any disclaimer, the term of this patent is extended or adjusted under 35 U.S.C. 154(b) by 465 days.

(21) Appl. No.: 16/348,694

(22) PCT Filed: Nov. 9, 2017

(86) PCT No.: PCT/JP2017/040363
§ 371 (c)(1),
(2) Date: Jul. 8, 2019

(87) PCT Pub. No.: WO2018/088458
PCT Pub. Date: May 17, 2018

(65) Prior Publication Data
US 2019/0322784 A1    Oct. 24, 2019

(30) Foreign Application Priority Data
Nov. 10, 2016   (JP) .............................. JP2016-219923

(51) Int. Cl.
| C08F 220/58 | (2006.01) |
| C09D 133/26 | (2006.01) |
| C08F 220/26 | (2006.01) |
| C08J 3/28 | (2006.01) |

(52) U.S. Cl.
CPC .......... *C09D 133/26* (2013.01); *C08F 220/26* (2013.01); *C08F 220/58* (2013.01); *C08J 3/28* (2013.01)

(58) Field of Classification Search
CPC .. C08F 220/58; C08F 230/085; C09D 133/26; C09D 143/04
See application file for complete search history.

(56) References Cited

U.S. PATENT DOCUMENTS

| 2008/0254375 A1* | 10/2008 | Hayashida ............... G03F 7/027 |
| | | 430/2 |
| 2015/0267159 A1* | 9/2015 | Kishioka ............... G03F 7/0757 |
| | | 435/180 |
| 2016/0102213 A1* | 4/2016 | Hayashi ................ A61L 17/145 |
| | | 428/522 |
| 2016/0312040 A1* | 10/2016 | Qiu ........................ C09D 5/165 |

FOREIGN PATENT DOCUMENTS

| JP | H02-245181 | 9/1990 |
| JP | H03-007576 | 1/1991 |
| JP | H05-176753 | 7/1993 |
| JP | 2009-065945 | 4/2009 |
| WO | 2014/058061 | 4/2014 |

OTHER PUBLICATIONS

Kitano et al., "Molecular Recognition at the Exterior Surface of a Zwitterionic Telomer Brush", Langmuir, 26(9), p. 6767-6774 (2010).
Suzuki et al., "Silica particles coated with zwitterionic polymer brush: Formation of colloidal crystals and anti-biofouling properties in aqueous medium", Colloids and Surfaces B: Biointerfaces, 84, p. 111-116 (2011).
Suzuki et al., "Carboxymethylbetaine copolymer layer covalently fixed to a glass substrate", Colloids and Surfaces B: Biointerfaces, 94, p. 107-113 (2012).
Matsuoka et al., "A design of low shrinkage acrylate and the mechanism of the hardening", RadTech Asia (2011), 2 pages.
Yoshioka et al., "A Design of Super Low-Shrinkage Acrylates and Its Curing Mechanism", Polymer Materials Forum (2010), 3 pages, with English translation.
Mitsukami et al., "Water-Soluble Polymers. 81. Direct Synthesis of Hydrophilic Styrenic-Based Homopolymers and Block Copolymers in Aqueous Solution via RAFT", Macromolecules, 34, p. 2248-2256 (2001).
Kitano et al., "Anti-biofouling Properties of a Telomer Brush with Pendent Glucosylurea Groups", Langmuir, 25(16), p. 9361-9368 (2009).
Skey et al., "Facile one pot synthesis of a range of reversible addition-fragmentation chain transfer (RAFTT) agents", Chem Commun, p. 4183-4185 (2008).
Lai et al., "Functional Polymers from Novel Carboxyl-Terminated Trithiocarbonates as Highly Efficient RAFT Agents", Macromolecules, 35, p. 6754-6756 (2002).
International Search Report and Written Opinion issued in PCT/JP2017/040363, dated Feb. 6, 2018, 19 pages, with English translation.

* cited by examiner

*Primary Examiner* — Karuna P Reddy
(74) *Attorney, Agent, or Firm* — Hamre, Schumann, Mueller & Larson, P.C.

(57) ABSTRACT

Disclosed are a cell culture substrate that can be modified from its cell-inadhesibleness to make it cell-adhesible, by a convenient and low-cost treatment, and particularly, a substrate that allows position-specific culture of one or more kinds of cells. The substrate has on its surface a layer made of a photomodifiable polymer that comprises a monomer, as component (A), represented by Formula (1):

$$\underset{O}{\overset{R1}{\underset{\|}{\diagup\hspace{-0.5em}\diagdown}}}\kern-1em\underset{}{\overset{H}{N}}\diagdown O\diagup\hspace{-0.3em}\left(\diagdown O\diagup\right)_{n}\hspace{-0.3em}R2 \quad (1)$$

wherein R1 denotes hydrogen or a methyl group, and R2 denotes an alkyl group having 1-22 carbon atoms, respectively, and n denotes an integer of 1-30, and a component (B) having a trialkoxysilyl group, which forms a layer.

7 Claims, 5 Drawing Sheets

MATERIAL FOR CELL PATTERNING USE

TECHNICAL FIELD

The present invention relates to the field of biomaterials, more specifically to a technology for arranging biological materials, such as proteins and cells, on a substrate surface in a position-specific manner, and in particular to a material that enables cell patterning, a substrate on which to culture cells in a state that they position-specifically adhere to it, and a method for production of the material.

BACKGROUND ART

At present, various kinds of animal and plant cells have come to be cultured, and new methods for culturing cells are being developed. Technologies of cell culture are utilized for such purposes as investigation of biochemical phenomena occurring in, and characteristics of, cells, production of useful substances, and the like.

Most cells, and in particular, many kinds of animal cells (except hematopoietic cells) are adhesion-dependent, i.e., grow by adhering to some object, and it is impossible to keep their viability for a long period in floating condition outside an organism. In order to culture such adhesion-dependent cells, a carrier is necessary to which the cells adhere. As such carriers, plastic petri dishes are generally employed to which a cell adhesion protein such as collagen or fibronectin is evenly applied. Such cell adhesion proteins are known to act on cultured cells by assisting cell adhesion and influence on their morphology.

Meanwhile, technologies have been reported by which cultured cells are arranged exclusively on very small areas of a substrate. Those technologies will enable utilization of cultured cells for artificial organs, biosensors, bioreactors and the like. As a method for arranging cultured cells, a method has been adopted in which a substrate having a surface on which is formed patterned zones having different adhesibleness for cells is employed, and cells are cultured on the surface to let them adhere exclusively to those zones of surface to which they can easily adhere, and thus the cells comes to be arranged in a predetermined form on the substrate.

For example, Patent Document 1 describes an application of charge retention medium on whose surface a pattern of static charge is provided, for such purposes as inducing neural cell to grow in a circuit like pattern. Further, Patent Document 2 describes an attempt to arrange cultured cells on a patterned surface prepared by photolithography using both cell-inadhesible and cell-adhesible, photosensitive hydrophilic polymers.

Furthermore, Patent Document 3 describes a cell culture substrate having a surface that is patterned with such a substance as influences cells' adhesion rate or morphology, such as collagen, and a method to produce that substrate by means of photolithography, thus realizing cell patterning by culturing cells on such a substrate and thereby letting more cells adhere to the part where such a substance as collagen is patterned, than to the other part.

Depending on an intended use, such patterning of positions for cell-adhesion may be required to achieve high resolution. Where patterning is carried out by photolithography using a photosensitive material as mentioned above, while a pattern could be provided at high resolution, it is required that a cell-adhesible material employed is a photosensitive one. It is often difficult to chemically modify biological polymers to provide them with such a photosensitivity, and the method therefore entails a drawback that scope of selectable cell-adhesible materials is very narrow. Still more, photolithography using a photoresist requires a treatment with a developing fluid and the like, which could in some cases have adverse effect on cell culture.

In addition, it is expected that a technology for position-specifically arranging such materials as proteins and cells (hereinafter comprehensively referred to as "biological materials") on a substrate surface will come to be utilized more than ever to a variety of situations including investigations in regenerative medicine, molecular biology, and cell biology, as well as development of new medicaments, and thus such a technology is required that can be applied to freely modify the surface of a substrate in an environment similar to one in a living body. Particularly, a technology is needed to modify an area of a substrate surface on the spot (in situ) in an environment where cells and proteins are present, among which such a technology is most required that is applicable to various biological materials exerting relatively limited influence on them. However, it still is highly difficult to prepare a surface that allows a position-specific control of various biological materials in an environment similar to one in a living body.

If such a surface can be prepared and utilized, it will enable evaluation of diverse correlations such as those between proteins and proteins, cells and cells, or cells and proteins, in a quasi-biological system. Since the cellular regulations occur not only by the actions of such physiological molecules, e.g., proteins and hormones, that are carried by circulating blood or bodily fluid (hereinafter referred to as "liquid factors") but also by interactions among cells, it is necessary to build an evaluation system mentioned above. While it is understood that cellular regulations are made through coordination of cell-cell interactions and actions of liquid factors, many remain unknown, such as the respective degrees of those two types of actions, and difference in their significance. In particular, it is highly important to understand "cell-liquid factor interaction" and "cell-cell interactions" among different kind of cells, in the field of cellular biology, and to understand regulations of cells and organs/tissues. However, evaluation of those interactions has not significantly progressed due particularly to the difficulty of constructing an in vitro experimental system that allows evaluation of those interactions separately and individually.

The present inventors have reported that a surface which is grafted with such a zwitterion-type polymer that is known not to correspond with biological molecules like proteins and cells, strongly suppresses adhesion of proteins and cells (Non-patent Documents 1 and 2). Further, it has also been found that selective patterning of cells (arrangement and immobilization) is possible by irradiation of a surface that carries a zwitterion-type polymer with an ion beam or ultraviolet light (Non-patent Document 3).

PRIOR ART DOCUMENTS

Patent Documents

[Patent Document 1] JPH02-245181 A
[Patent Document 1] JPH03-007576 A
[Patent Document 1] JPH05-176753 A Non-Patent Documents

[Non-patent Document 1] Kitano, H.; Suzuki, H.; Matsuura, K.; Ohno, K., Langmuir 2010, 26, 6767.

[Non-patent Document 2] Suzuki, H.; Murou, M.; Kitano, H.; Ohno, K., Colloids Surfaces B: Biointerfaces 2011, 84, 111.

[Non-patent Document 3] Suzuki, H.; Li, L.; Nakaji-Hirabayashi, T.; Kitano, H.; Ohno, K.; Matsuoka K; Saruwatari, Y., Colloids Surfaces B: Biointerfaces 2012, 94, 107.

SUMMARY OF INVENTION

Technical Problem

Against the above background, an objective of the present invention is to provide a cell culture substrate material that can be modified from its initial cell-inadhesibleness to make it cell-adhesible, by a convenient and low-cost treatment. Another objective of the present invention is to provide a substrate having a surface covered with such a material and allowing cell patterning, and a method for production of such a substrate. Still another objective of the present invention is to provide a substrate that allows easy patterning of multiple different kinds of cell populations without substantially damaging the cells, and a method for production of such a substrate. A still further objective of the present invention to provide such a substrate that further allows patterning cells in a manner that multiple different kinds of cell populations adjoin to one another, so as to enables separate and individual evaluation of cell-cell interactions and cell-liquid factor interactions in regulations of cellular activities, as well as a method for its production.

Solution to Problem

In the studies directed to the above objectives, the present inventors conceived of a unnoticed possibility that a polymer whose side chains can be modified with ultraviolet light having a wavelength less affecting biological materials in water could meet the above objectives, and of modification of a substrate surface using such a polymer. As a result of further studies based on the concept, the present inventors found that a substrate having a polymer layer on its surface formed using a (meth)acrylate-based monomer possessing such a polyethylene glycol moiety that can be cleaved by irradiation with electromagnetic wave like ultraviolet light having a certain wavelength, enables position-specific control of adhesion of cells and proteins to its surface by a convenient method, and completed the present invention after further investigations. Thus, the present invention provides what follows.

1. A photomodifiable polymer comprising, as component (A), a monomer represented by Formula (1),

[Chem. 1]

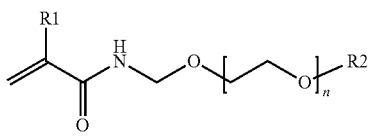

(1)

wherein R1 denotes hydrogen or a methyl group, and R2 denotes an alkyl group having 1-22 carbon atoms, respectively, and n denotes an integer of 1-30, and a component (B) having a trialkoxysilyl group.

2. The photomodifiable polymer according to 1 above, wherein each of the alkoxyl groups of the trialkoxysilyl group in component (B) is, independently, an alkoxyl group having 1-4 carbon atoms.

3. The photomodifiable polymer according to 1 or 2 above, wherein the trialkoxysilyl group of component (B) is located at the end of the polymer chain that comprises a portion composed of polymerized multiple components (A).

4. The photomodifiable polymer according to 1 or 2 above, wherein the component (B) is represented by Formula (2):

[Chem. 2]

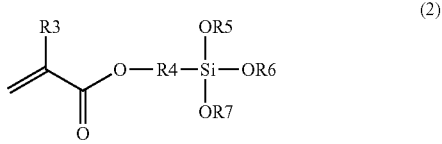

(2)

wherein R3 denotes hydrogen or a methyl group; R4 denotes an alkylene group having 1-8 carbon atoms; and each of R5, R6 and R7 independently denotes an alkyl group having 1-4 carbon atoms, respectively.

5. The photomodifiable polymer according to 4 above comprising the component (A) represented by Formula (1) and the component (B) represented by Formula (2), wherein the molar ratio of component (A):component (B) is 75:25 to 98:2.

6. The photomodifiable polymer according to 3 above, wherein the polymer has a structure represented by Formula (3):

[Chem. 3]

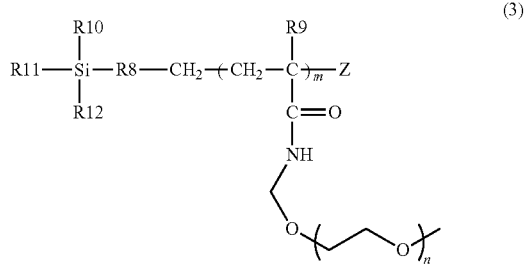

(3)

wherein R8 denotes an aromatic group that may have one or more saturated hydrocarbon groups having 1-4 carbon atoms; R9 denotes hydrogen or a methyl group; each of R10, R11 and R12 independently denotes an alkoxyl group having 1-4 carbon atoms; and Z denotes a group —S—C(S)—S—R13, wherein R13 denotes an alkyl group having 1-6 carbon atoms.

7. A cell culture substrate comprising a base material and a polymer layer formed on the surface thereof, wherein the polymer layer consists of the photomodifiable polymer according to one of 1-6 above, and is held on the base material with a bond produced by a reaction between the trialkoxysilyl group of the component (B) and the base material.

8. The cell culture substrate according to 7 above, wherein the base material consists of glass, ceramic, metal, or of a resin treated with a glass-based primer.

9. A method for producing a cell culture substrate, wherein the method comprises applying the photomodifiable polymer according to one of 1-5 above to the surface of a base material.

10. A method for producing a cell culture substrate, wherein the method comprises copolymerizing, as component (A), a monomer represented by Formula (1):

[Chem. 4]

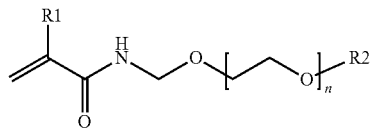

(1)

wherein R1 denotes hydrogen or a methyl group, and R2 denotes an alkyl group having 1-22 carbon atoms, respectively, and n denotes an integer of 1-30, and, as component (B), a monomer represented by Formula (2):

[Chem. 5]

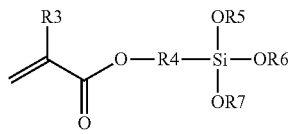

(2)

wherein R3 denotes hydrogen or a methyl group; R4 denotes an alkylene group having 1-8 carbon atoms; and each of R5, R6 and R7 independently denotes an alkyl group having 1-4 carbon atoms, respectively, on the base material.

11. The method according to 10 above, wherein the base material consists of glass, ceramic, metal, or of a resin treated with a glass-based primer.

12. A method for coculturing different kinds of cell populations in the state that they adhere to the same substrate in the areas thereof that respectively correspond to the cell populations, comprising the steps of irradiating a first area of the cell culture substrate according to 7 or 8 above with ultraviolet light to modify the first area, and then culturing a first kind of cells on the substrate to let the population of the first kind of cells adheres the first area, and the steps of irradiating a second area of the substrate different from the first area with ultraviolet light to modify the second area, and then culturing a second kind of cells different from the first kind of cells on the substrate to let the population of the second kind of cells adhere to the second area.

Effects of Invention

The surface of the cell culture substrate of the present invention defined above, when untreated, does not allow cells adhere thereto under a condition similar to those in the living body. However, by irradiating it with ultraviolet light, the polymer on its surface is modified (polyethylene glycol moieties cleaved) into a surface that allow cells to adhere thereto. Thus, it enables culturing a single kind of cells in a state that they adhere exclusively to a particular area, just by a very simple and low cost treatment in advance, such as irradiation with ultraviolet light, through a photomask or the like, to modify merely the intended area of the substrate surface to which cells are to adhere.

Further, in the state with a certain kind of cells having adhered only to a particular area as mentioned above, it is also possible, by irradiating some other area (whole or part of the remaining area) with ultraviolet light, to culture new cells (e.g., another kind of cells) in a state that they adhere to the newly irradiated area. In doing this, for example, it is also permitted to irradiate the entire substrate with light having a wavelength that would not substantially affect those cells which have already adhered to the substrate (e.g., ultraviolet having a wavelength of 360-370 nm). In this case, as the polymer on the substrate surface surrounding the area to which cells have already adhered will also be modified, another kind of cells added thereafter and cultured would adhere to the newly modified area of the substrate and spread there, thereby forming a new population of adhering cells that adjoins the already present population of adhering cells.

Furthermore, as needed, it is also possible to culture different kinds of cells in the state that they adhere to three or more respective areas of the substrate surface, by sequentially conducting three or more respective steps each of which comprises irradiating one of different areas of the substrate surface, seeding cells, and culturing them.

Thus, the present invention enables evaluation of cell-cell interactions and cell-liquid factor interactions separately and independently, by utilizing multiple cell populations adjoining each other on the same substrate, and also enables utilization of such evaluation in research and development of new medicaments and the like.

DESCRIPTION OF EMBODIMENTS

Figure 1:
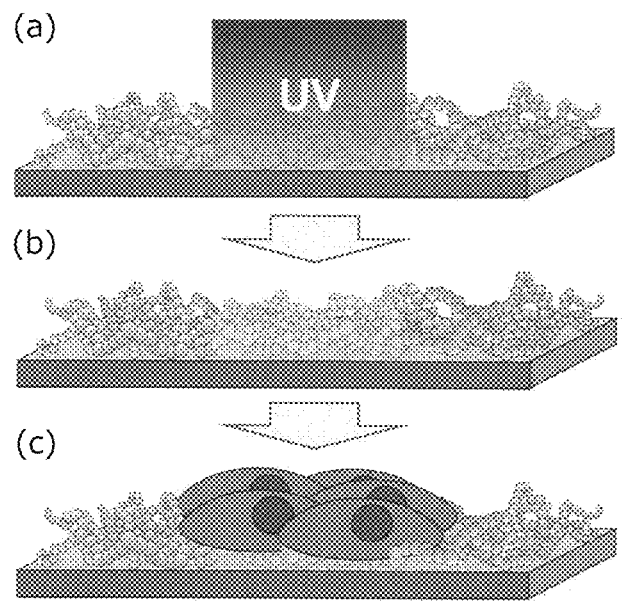
FIG. 1 is a schematic illustration of modification of a particular area of cell culture substrate by irradiation with ultraviolet light directed to it, and adhesion of cells to the area.

In the present invention, the monomer as component (A) represented by Formula (1):

[Chem. 6]

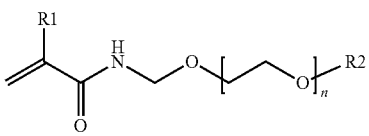

(1)

wherein R1 denotes hydrogen or a methyl group, and R2 denotes an alkyl group 1-22 carbon atoms, respectively, and n denotes an integer of 1-30, can be synthesized by a method described in, for example, JP Patent No. 5410034, JP Patent No. 541902, JP Patent No. 5198845, or JP2012-144684 A. The number of carbon atoms of R2 may be, for example, 1, 2, 3, 4, 6, 10, 18, 20, or 22. The integer n is preferably 1-25, more preferably 2-20, and still more preferably 3-10.

In the present invention, in the case where a monomer as component (B) represented by Formula (2):

[Chem. 7]

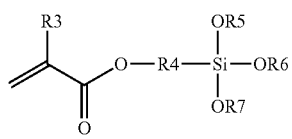

(2)

wherein R3 denotes hydrogen or a methyl group; R4 denotes an alkylene group having 1-8, more preferably 1-6, and still more preferably 1-4 carbon atoms; and each of R5, R6 and R7 independently denotes an alkyl group having 1-4, more preferably 1-3 carbon atoms, respectively, preferable examples thereof include, but are not limited to, trimethoxysilylpropyl (meth)acrylate, triethoxysilylpropyl (meth)acrylate, triisopropoxysilylpropyl (meth)acrylate, trimethoxysilylethyl (meth)acrylate, triethoxysilylethyl (meth)acrylate, and triisopropoxysilylethyl (meth)acrylate.

In the present invention, in the case where the photomodifiable polymer comprises a component (A) represented by Formula (1) and a component (B) represented by Formula (2), their molar ratio, component (A):component (B), is preferably 75:25 to 98:2, more preferably 80:20 to 98:2, and still more preferably 85:15 to 95:5.

In the present invention, the base material to which the photomodifiable polymer of the present invention is applied is selected from the group consisting of, e.g., glass, ceramic, metal, or a resin having a surface treated with a glass-based primer. In the case where the base material is glass, examples of preferable glass include silica glass (soda-lime glass, borosilicate glass, fused quarts, and the like). Further, any one of resins may be used as desired insofar as its surface has been treated with a glass-based primer. Those include, for example, polyethylene, polypropylene, polystyrene, polyvinyl chloride, nylon, polyurethane, polyurea, polylactic acid, polyglycolic acid, polyvinylalcohol, polyvinyl acetate, poly(meth)acrylic acid, poly(meth)acrylate derivatives, polyacrylonitrile, poly(meth)acrylamide, poly(meth)acrylamide derivatives, polysulfones, polycarbonate, cellulose, cellulose derivatives, polysilicones These resins may be used singly or in combination.

In the present invention, there is no particular limitation as to a method employed to provide the surface of a base material with a layer of photomodifiable polymer. For example, it is possible to prepare a polymer first, which then is applied to the surface of a base material in any manner such as by daubing or spraying to form a coating membrane, or alternatively, it is also possible to apply a liquid containing monomers and an initiator, and then let them copolymerize with heat or light to form a coating membrane.

The photomodifiable polymer of the present invention can be obtained by, for example, allowing components including monomers selected as component (A) and component (B,) respectively, to copolymerize in water or an organic solvent. Namely, that can be done by dissolving a desired amount of monomers in purified water or an organic solvent, adding a polymerization initiator with stirring, and letting copolymerization take place in an inert gas atmosphere. In addition, when needed, a chain-transfer complex may be used. In preparing a liquid containing monomers and an initiator, employment of water or an organic solvent is not necessary as a solvent, depending on the monomers selected.

There is no particular limitation as to what is employed as a an organic solvent, and any conventional solvent generally used in solution polymerization may be employed as desired, i.e., alcohols such as methyl alcohol, ethyl alcohol, isopropyl alcohol, ethylene glycol, propylene glycol, and the like; ketones such as acetone, methyl ethyl ketone, and the like; ethers such as diethyl ether, tetrahydrofuran, and the like; aromatic compounds such as benzene, toluene, xylene and the like; hydrocarbons such as n-hexane, cyclohexane, and the like; acetic acid esters such as methyl acetate, ethyl acetate, and the like; and water.

Besides, in the case where copolymerization is induced in water or an organic solvent, it is preferable to adjust the concentration of polymerizing components to about 10-80 wt %.

There is no particular limitation as to a polymerization initiator usable in the present invention, either. For example one of common azo polymerization initiators or persulfate polymerization initiators can be selected and used as desired, such as azoisobutyronitrile (AIBN), azoisomethyl butyrate, azobisdimethylvaleronitrile, benzoyl peroxide, potassium persulfate, or ammonium persulfate. Further, as a photopolymerization initiator, one of those photoinitiators can be used, such as benzophenone derivatives, phosphine oxide derivatives, benzoketone derivatives, phenyl thioether derivatives, azide derivatives, diazo derivatives, disulfide derivatives, and the like.

The amount of a polymerization initiator can generally be, but is no limited to, about 0.01-5 parts by weight to 100 parts by weight of polymerizing components.

There is no particular limitation as to the above-mentioned chain-transfer complex usable in the present invention. For example, compounds having a mercaptan group such as lauryl mercaptan, dodecyl mercaptan and thioglycerol; and inorganic salts such as sodium hypophosphite, and sodium bisulfate can be used. The amount of such chain-transfer agents can generally be, but not limited to, about 0.01-10 parts by weight to 100 parts by weight of polymerizing components.

Figure 2:
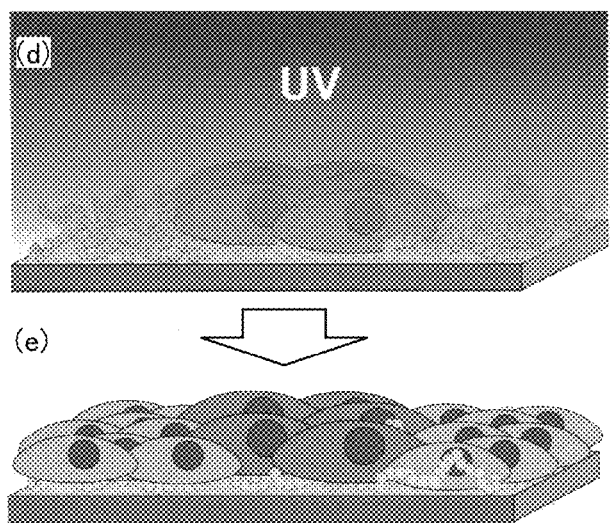
FIG. 2 is a schematic illustration of modification of another area of the cell culture substrate by irradiation with ultraviolet light directed to it, and adhesion of an additional, another kind of cells to the area.

In the present invention, as shown in FIGS. 1-2 specifically, a substrate having a polymer layer constructed on its surface is irradiated with ultraviolet light, at first in only a certain area to modify the area alone to make it cell adhesible, and a certain kind of cell are induced to adhere there. Then, a second irradiation with ultraviolet light in a manner that inflicts no substantial damage to the already adhering cells, would modify the polymer layer in the area with no adhering cells into a cell adhesible surface, and thus a second kind of cells could be brought into contact with the cell adhesible surface newly prepared, to let them adhere to it. In order to carry out a second ultraviolet irradiation without inflicting substantial damage to the cells, ultraviolet light having such wavelength can be chosen (e.g., 360-370) and used to irradiate the whole substrate including the area to which the cells already adhere, or alternatively, irradiation can be carried out of unirradiated area only, through a shield such as a photomask, for example but without limitation, and other convenient methods can be chosen as desired in accordance with the purpose or conditions of culture.

In the case where different kinds of cells are cultured on the substrate surface while keeping their respective position-specific adhesion, they are thought to be regulated by cell-cell interactions between different kind of cells, and by the effects of secreted factors, in the interface region between different kinds of cells, while cells locating in an area where different kinds of cells are not in contact, are thought to be regulated solely by effects of circulating factors such as hormones and the like. Therefore, use of a cell culture substrate with which different kinds of cells are patterned on the same surface as mentioned above, enables simultaneous evaluation of the above two kinds of actions regulating cell activities, regarding their degrees, difference in significance, and the like, in a single culture system.

EXAMPLES

While the present invention will be described in further detail below with reference to Examples, it is not intended that the present invention be limited to the Examples.
(Materials)
4-(Chloromethyl)phenyltrimethoxysilane (CMPTS): AZmax Co.
Microscopic slide glass: Matsunami Glass Ind. Ltd., used by cutting into 26 mm×22 mm×1 mm 4,4'-Azobis(4-cyanopentanoic acid) (V-501, 98.0%): Wako Pure Chemical Industries, Ltd.

(Methoxypolyethylene glycol)acrylamide (MEGAm): Osaka Organic Chemical Industry Co., Ltd.

[Chem. 8]

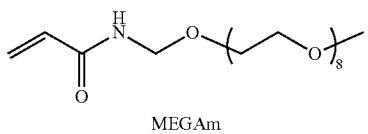

MEGAm (Example 1) Formation and Evaluation of Polymer Layer—1

1. Preparation of RAFT Agent and a Precursor of RAFT Agent (1) Synthesis of a RAFT Agent
(n-Butylsulfanylthiocarbonylsulfanyl 2-Methylpropionic Acid) (BSTMPA)

[Chem. 9]

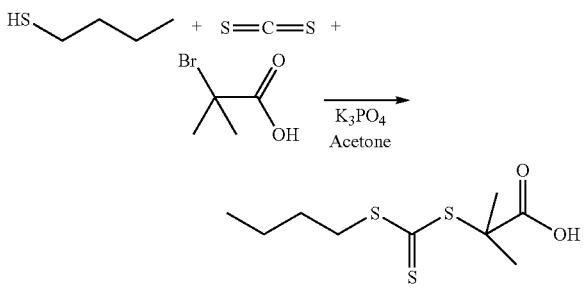

In 32.0 mL of acetone was dissolved 4.25 g (20 mmoL) of $K_3PO_4$, and stirred for 30 minutes. To this reaction solution was added 2.14 mL (20 mmoL) of 1-butanethiol and stirred for 10 minutes, and then 3.6 mL (60 mmoL) of carbon disulfide was added and stirred for 10 minutes. Following further addition of 3.34 g (20 mmoL) of 2-bromo-2-methylpropionic acid, reaction was allowed to proceed for 18 hours. After completion of the reaction, precipitated salt was removed by suction filtration, and the filtrate was concentrated in an evaporator in vacuo to remove acetone. Separation and isolation were carried out using a silica gel column. As solvent, hexane/ethyl acetate=10:1 (v/v) was used. The eluate with which a spot (Rf=0.13) corresponding to the product was confirmed on TLC was collected, concentrated in vacuo, and after addition of hexane, stored in a refrigerator to allow recrystallization to take place. Precipitated crystals were collected by suction filtration, and dried in a desiccator to give the product as yellow powder.

Yield: 840 mg (17%), $^1$H NMR (400 MHz, CDCl$_3$) δ: 0.94, (t, 3H, —C$\underline{H}_3$)); 1.43 (6, 2H, —C$\underline{H}_2$—CH$_3$); 1.66 (5, 2H, —CH$_2$—C$\underline{H}_2$—CH$_2$—); 1.73 (s, 3H×2, CC$\underline{H}_3$); 3.30 (t, 2H, —S—C$\underline{H}_2$—) ppm (2) Synthesis of RAFT Precursor (Dithiobenzoic Acid: SDTB)

[Chem. 10]

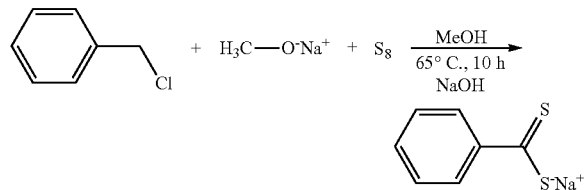

In 3.6 mL of dehydrated methanol was dissolved 1.08 g (0.020 moL) of sodium methoxide, and after addition of 640 mg (0.020 moL) of elemental sulfur, the mixture was stirred under nitrogen gas bubbling. To this reaction mixture was added 1.14 mL (0.010 moL) of benzyl chloride dropwise over 30 minutes, and reaction was allowed to proceed for 10 hours at 65° C. After completion of the reaction and ice-water immersion which followed, precipitated crystals were removed by suction filtration, and the solvent was removed by in vacuo concentration. After addition of 10 mL of water and further suction filtration, 4 mL of diethyl ether was added to the filtrate, and put to separation treatment. Additional separation treatment was carried out two times in the same manner, and to the collected water layer were added 4 mL of diethyl ether and 5 mL of 1 M HCl, and the mixture was put to separation treatment. To the collected diethyl ether layer were added 6 mL of water and 1 M NaOH, and the mixture was put to separation treatment. After this separation treatment, a separation treatment in which diethyl ether was added to the collected water layer, and a separation treatment in which water and 1 M NaOH were added to the collected diethyl ether, were further carried out two times, respectively, in the same manner. The solvent was removed from the collected water later by in vacuo concentration, and acetone was added. After the salts thus precipitated were removed by suction filtration, the filtrate was concentrated in vacuo, and then dried in vacuo to give the product as a red-brown powder. Yield: 542 mg (31%)

2. Construction of Polymer Brush Using RAFT Polymerization (1) Formation of 4-(Chloromethyl)Phenyltrimethoxysilane (CMPTS) Self-Assembled Monolayer (SAM) on the Surface of Glass Substrate Plate Forty mL of 2 v/v % CMPTS solution was prepared using 4-(chloromethyl)phenyltrimethoxysilane (CMPTS) and purified toluene. In this was immersed a glass substrate plate (22 mm×26 mm) that had been pre-washed with water (UltraPure water, 18 MO, Millipore Systems, the same applies hereinafter), methanol, and acetone, and then washed in a UV/ozone washing machine (UV/ozone cleaner UV253E, Filgen Inc.), and after nitrogen substitution, the lid was closed and the reaction was allowed to proceed for 15 hours at 80° C. After conditioned with the silane coupling agent, the plate was rinsed three times in purified toluene, and then dried with nitrogen gas.

(2) Preparation of RAFT Agent on Silane Coupling Agent-Treated Surface of Glass Substrate Plate Using the SDTB that had been synthesized and THF, 40 mL of 20 g/mL SDTB solution was prepared. In this was immersed the glass substrate plate that had been treated with the silane coupling agent (CMPTS), and reaction was allowed to take place. After left undisturbed for one hour to let SDTB react, the plate was rinsed three times in methanol, and dried with nitrogen gas.

(3) Construction of PMEGAm Brush by RAFT Polymerization

In a sample bottle were placed a magnetic stir bar and a substrate plate stand (made of Teflon™), and 2.69 mL (8 mmoL) of MEGAm, 2.24 mg (0.008 mmoL) of V-501, and 9.36 mg (0.04 mmoL) of BSPMTA were put there and dissolved in 37.3 mL of ethanol. Further, the glass substrate plate having a surface on which the self-assembled monolayer of RAFT agent was formed was placed in it, and then nitrogen gas was infused for 30 minutes to bring the reaction system completely in nitrogen atmosphere. Following this, reaction was initiated by immersing the sample bottle in a water bath at 70° C. After a 24-hour reaction, the reaction vessel was immersed in ice water to terminate the reaction. The substrate plate was taken out and washed alternately with water and methanol, and dried with nitrogen gas.

[Chem. 11]

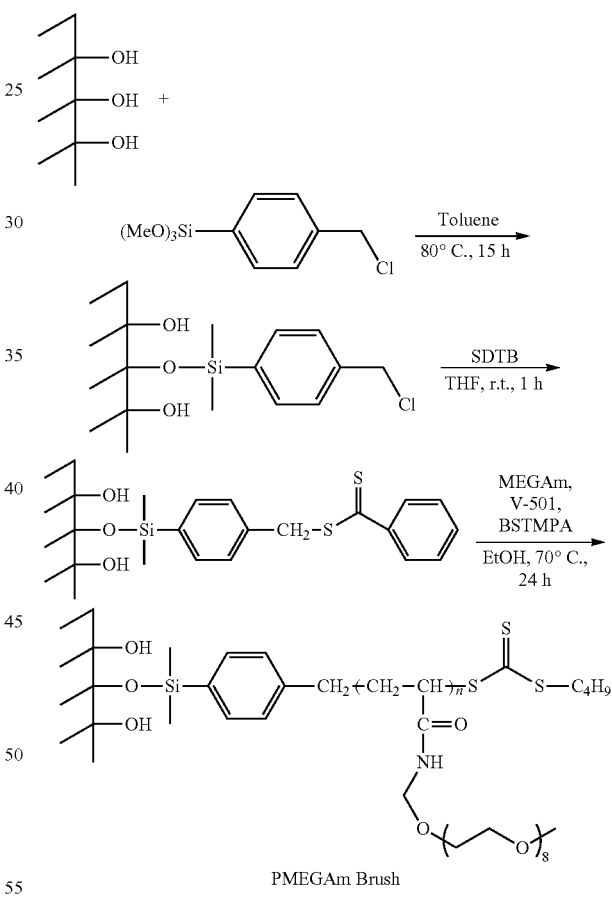

PMEGAm Brush

3. Evaluation of Wettability by Contact Angle Measurement

In order to evaluate the wettability of the surface, water contact angle was measured using a contact angle meter (FACE Contact angle meter CA-D, Kyowa Interface Science Co., Ltd.). In the case of droplet method for measuring a substrate plate in a dry state, 6 points per substrate plate was evaluated based on the sum of angles at 24 and 33 seconds after 3-4 of water was contacted with the sample at room temperature, and their mean value was employed as the measurement.

4. Evaluation of Membrane Thickness by Ellipsometry

The thickness of the membrane of the sample in a dry state was evaluated using an ellipsometer (M-2000U, J.A. Woollam Co. Inc., USA). Measurement was performed at room temperature in the air, in the setting of incident angle: 70°, wavelength: from 242 nm to 999 nm, index of refraction of sample layer: 1.49 (value for poly(methyl methacrylate)).

5. Surface Modification by UV Irradiation of PMEGm Brush-Constructed Substrate Plate (1) Surface Modification by UV Irradiator (300-400)

The dry state surface of PMEGAm brush-constructed substrate plate was irradiated with UV light (irradiation intensity: 731 mW/cm$^2$, irradiation time: 30 minutes, irradiation diameter: 15 mm, wavelength: 300-400 nm, condenser lens: SFH lens) using a UV irradiator (SP-9, Ushio Inc.), and washed with water and methanol, and then sterilized by immersion in 70% ethanol solution and air drying in a clean bench. Aqueous solution of 50 µg/mL poly-L-ornithine (PLO) (MW: 30000-70000) was then mounted and left undisturbed for one hour. After removal of the PLO solution, the substrate plate was washed once with sterilized water, and 25 µg/mL laminin/PBS (LN) solution was mounted and left undisturbed for one hour. The substrate plate was washed twice with PBS and immersed in the culture medium until seeding of cells.

(2) Surface Modification by Fluorescence Microscope (360-370 nm)

The surface of PMEGAm brush-constructed substrate plate immersed in a solution was irradiated with the excitation light (360-370 nm, 320 mW/cm$^2$, lens: 20×field lens) from an inverted fluorescence microscope (IX71, Olympus Corp.) for 30 minutes, washed with water and methanol, and then sterilized by immersion in 70% ethanol solution and air drying in a clean bench. Aqueous solution of poly-L-ornithine (PLO) was then mounted and left undisturbed for one hour. After removal of the PLO solution, the substrate plate was washed once with sterilized water, and a laminin solution (a protein of extracellular matrix) was mounted and left undisturbed for one hour. The substrate plate was washed twice with PBS and immersed in the culture medium until seeding of cells.

[Chem. 12]

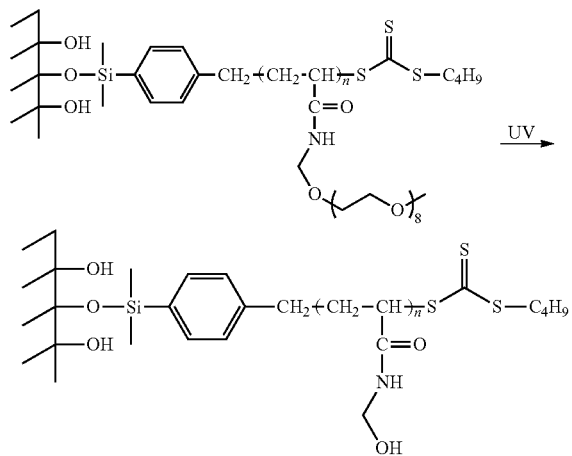

6. Seeding of Neural Stem/Progenitor Cells onto the Substrate Plate Having Modified Surface Fischer rat embryo (embryo 14) striatum-derived stem/progenitor cells (NSPC) (passage 1) that had been suspension-cultured (neurosphere culture) to let multiply, were treated with 0.05% trypsin-0.2 mM EDTA to prepare single cells. Onto the PMEGAm brush-constructed substrate plate having the surface modified using the UV irradiator or the fluorescence microscope, were seeded NSPC at a cell density of 5×10$^4$/cm$^2$, and cultured for three days at 37° C., 5% CO$_2$, in a 1:1 mixture solution of Dulbecco's Modified Eagle medium/nutrient mixture F-12 (DMEM/F12) containing 3 Glutamax (diamino acid, Gln-Ala), 5 µg/mL of heparin, 100 unit/mL of penicillin, 2% B27 (serum supplement), 20 ng/mL of basic fibroblast growth factor (bFGF) and 20 ng/mL of epidermal growth factor (EGF).

Figure 3:
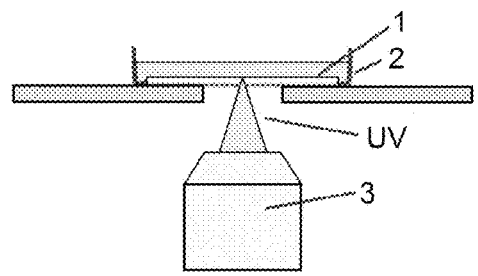
FIG. 3 is a schematic illustration of the method for irradiation of the substrate with ultraviolet light.

7. Surface modification with UV irradiation for cell-adhering substrate plate, and evaluation of cell spreading in irradiated area NSPC were cultured for 14 days on a PMEGAm brush-constructed substrate plate that had been irradiated under the same condition as in 6(2) above. The cell culture substrate plate was irradiated with excitation light (360-370 nm) from the inverted fluorescence microscope for a certain length of time. The irradiated area was a border area between the cell adhering and the non-adhering areas. As shown in FIG. 3, irradiation was performed from backside of the cell culture substrate plate while continuing culture. After the irradiation treatment, the culture medium was exchanged and culture was continued.

Besides, in the case where the inverted fluorescence microscope was employed, irradiation with UV light was to be made from backside of the substrate plate. Thus, in order to examine whether irradiation from the bottom of the substrate plate is feasible, evaluation of transmittance to ultraviolet light of the glass microscopic slide and the polystyrene petri dish (TCPS) employed in culturing cells was performed on an ultraviolet visible spectrophotometer (Lamda 950 UV/Vis Spectrometer, Perkin Elmer).

8. Results (1) Evaluation of Polymer Brush by RAFT Polymerization

Table 1 shows the results of evaluation of the surface condition of the substrate plate at each reaction stage of preparation of PMEGAm brush-constructed substrate plate, in terms of contact angle of droplets and change in membrane thickness. Compared with the contact angle of 5.2° with untreated glass, it was found to be 63.7° and 62.0° following modification with CMPTS and SDTB, respectively, indicating drastic slump in hydrophilicity. This is because the surface of untreated glass having OH groups was converted to a more hydrophobic, aromatic ring-retaining surface, indicating the surface of the substrate plate was modified with the RAFT agent.

Further, following polymerization of MEGAm, wettability was found increased both with MEGAm tDP 50 and MEGAm tDP 200. Considering a report that the contact angle with PEG is around 40° (Benhabbour, S. R. et al., Macromolecules, 2008, 13, 4817) and the effect of the RAFT agent present at the end of polymer brush, the above results indicates that PMEGAm brush was constructed on the surface of the substrate plate. Furthermore, increased thickness of the membrane was also observed with MEGAm tDP50 (thickness of the membrane not measured with MEGAm tDP 200).

TABLE 1

Contact angle to the substrates and thickness of the membrane

|  | Sessile droplet (angle) | Thickness (mm) |
|---|---|---|
| Untreated glass | 5.2 (±0.2) | — |
| CMPS | 67.3 (±0.5) | 0.88 (±0.030) |
| SDTB | 62.0 (±0.7) | 0.96 (±0.073) |
| PMEGAm (tDP 50)[a] | 46.9 (±0.4) | 1.80 (±0.008) |
| PMEGAm (tDP 200)[b] | 42.7 (±0.2) | Not measured |

[a] Molar ratio of monomer:initiator:RAFT agent = 250:1:5
[b] Molar ratio of monomer:initiator:RAFT agent = 1000:1:5

(2) Evaluation of Cell Adhesin Behavior Following the Surface Modification of PMEGAm Brush-Constructed Substrate Plate (a) Evaluation of Surface Modification by UV Irradiator (300-400 nm)

Figure 4:
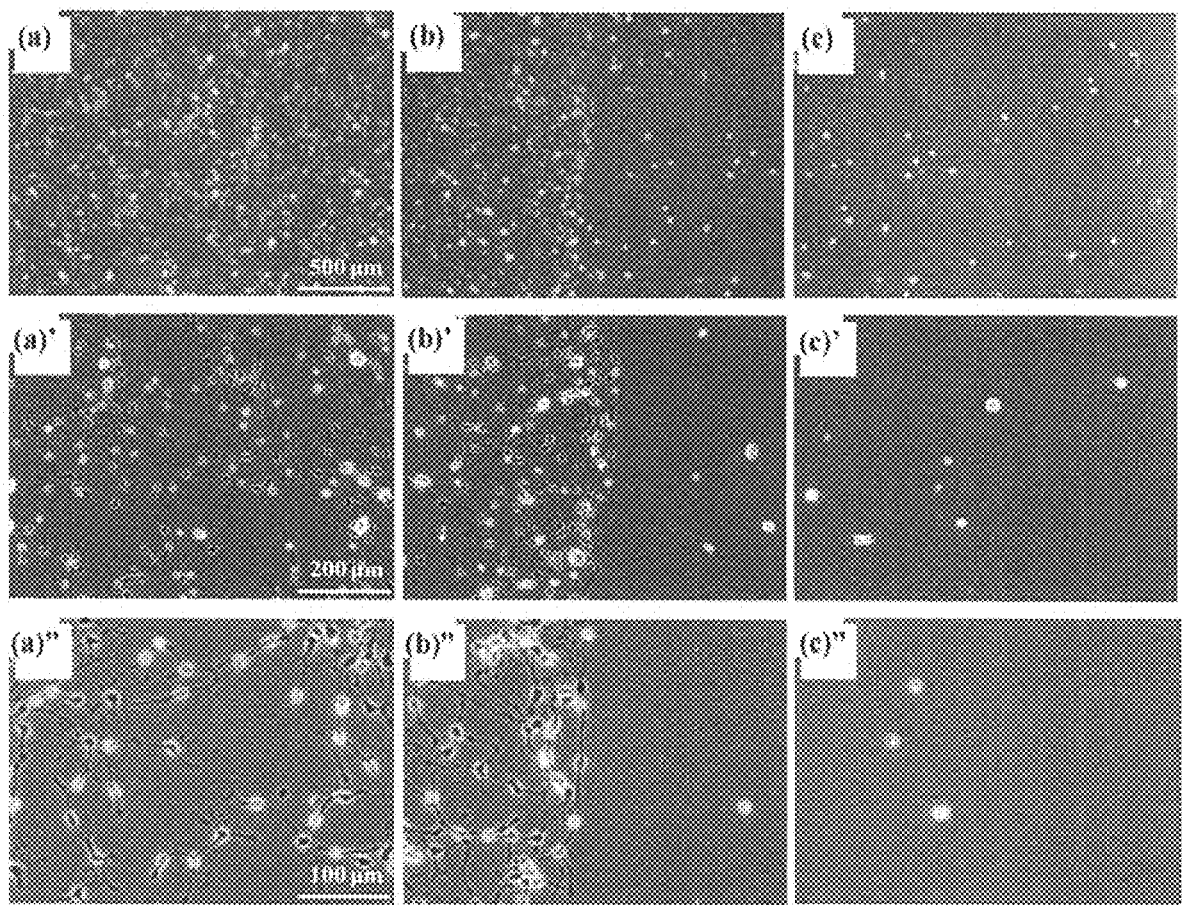
FIG. 4 is a set of microphotographs showing the state of cell adhesion after a one-day cell culture on the cell-culture substrate of Example 1 that had been irradiated in a particular area with ultraviolet light (300-400 nm). The left column shows the irradiated area, the right column the unirradiated area, and the middle column an intermediate area between the two. The bars in the photographs correspond to 500 μm, 200 μm, and 100 μm, respectively, from the top.
Figure 5:
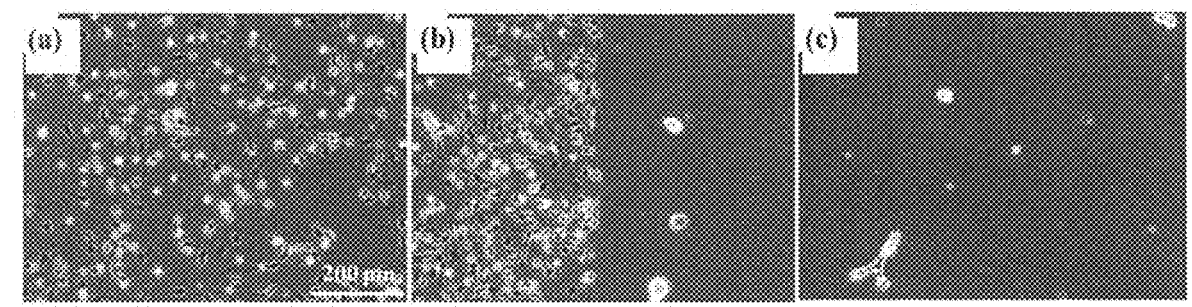
FIG. 5 is a set of microphotographs showing the state of cell adhesion after a 3-day cell culture on the cell culture substrate of Example 1 that had been irradiated with ultraviolet light (300-400 nm) in a particular area of it. The left column shows the irradiated area, the right column the unirradiated area, and the middle column an intermediate area between the two. The bar in a photograph corresponds to 200 μm.

Evaluation was made of cell adhesion to the PMEGAm brush-constructed surface that had undergone UV irradiation (731 mW/cm$^2$, 30 minutes, irradiation diameter: 15 mm). FIG. 4 shows a microphotograph of PMEGAm surface after a one-day cell culture, and FIG. 5 that of after a three-day cell culture. In FIG. 4 and FIG. 5, (a), (a)', and (a)" show microphotographs of the irradiated area; (b), (b)', and (b)" of border area between the irradiated and the unirradiated areas, (c), (c)', and (c)" of the unirradiated area.

On the surface of PMEGAm after the one-day cell culture, very few cells were found adhering to the unirradiated area, and no spreading of adhering cells was observed, indicating that the PMEGAm brush gave a surface that had a cell adhesion-suppressing capacity (FIG. 4(c)). In contrast, a number of cells were observed adhering to the UV-irradiated area (FIG. 4(a)), and adhering cells were also found spreading, indicating that the cell adhesion-suppressing capacity of the PMEGAm brush was lost by UV irradiation. Further, in the border region between the UV-irradiated and the unirradiated areas, there was found a clear border between the cell adhering and the non-adhering areas (FIG. 4(b)).

Increase in the number of adhering cells and spreading of adhering cells in the UV-irradiated area were more markedly observed on the PMEGAm surface cultured for three days than that on the surface cultured for one day. Besides, no cell adhesion or spreading was observed in the unirradiated area.

PEG is known to have a cell adhesion-suppressing capacity, and PMEGAm has a PEG in its side chains. In addition, it is also thought to be reflecting an excluded volume effect by the polymer brush, that the PMEGAm brush-constructed surface exhibited cell adhesion-suppressing capacity. It is considered that by irradiation of the PMEGAm brush-constructed surface with UV light, however, the PEGs in the side chains were cleaved and thereby the surface was modified to allow cell adhesion. The above results demonstrates that by irradiating a PMEGAm brush-constructed surface with UV light, it is possible to modify the PMEGAm surface and realize position-specific cell adhesion.

Figure 6:
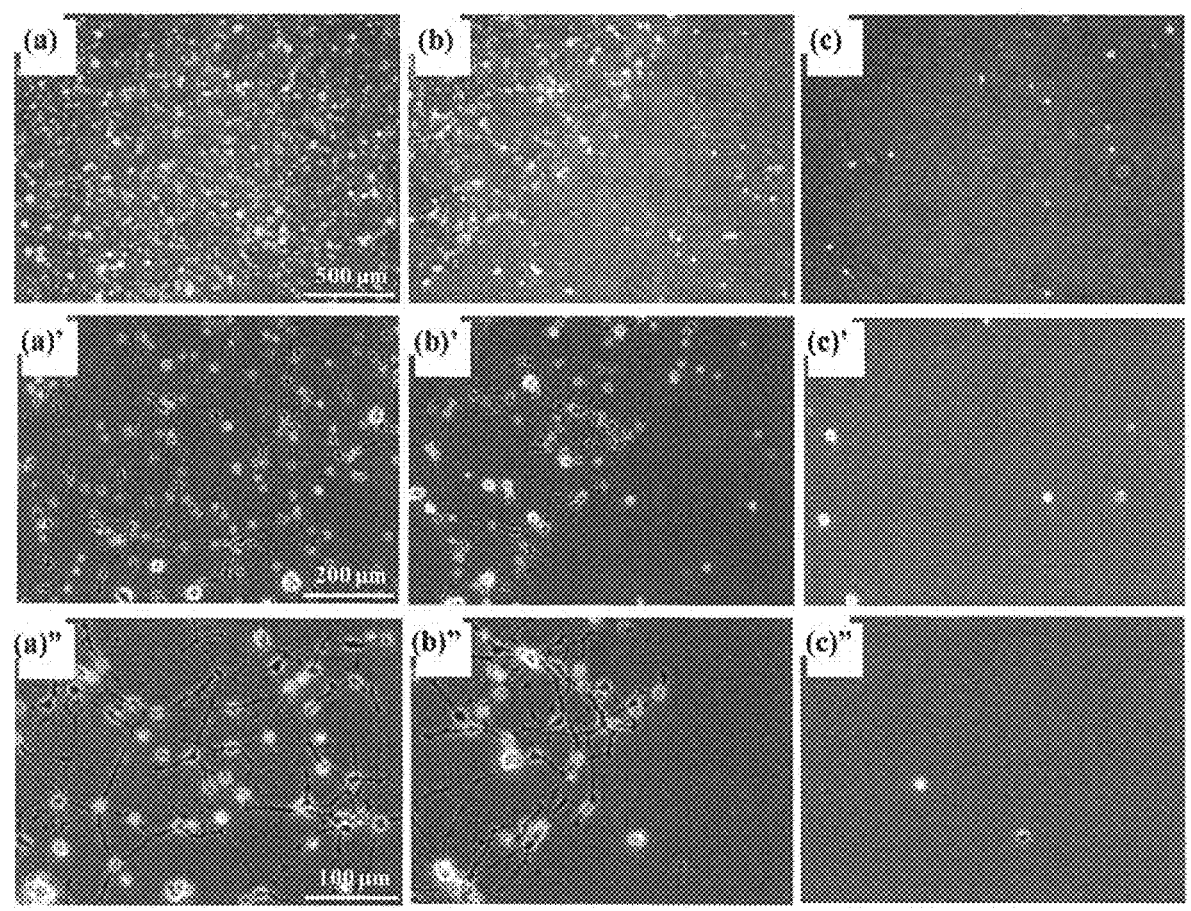
FIG. 6 is a set of microphotographs showing the state of cell adhesion after a one-day cell culture on the cell culture substrate of Example 1 that had been irradiated with ultraviolet light (360-370 nm) in a particular area of it. The left column shows the irradiated area, the right column the unirradiated area, and the middle column an intermediate are between the two. The bars in the photographs correspond to 500 μm, 200 μm, and 100 μm, respectively, from the top.
Figure 7:
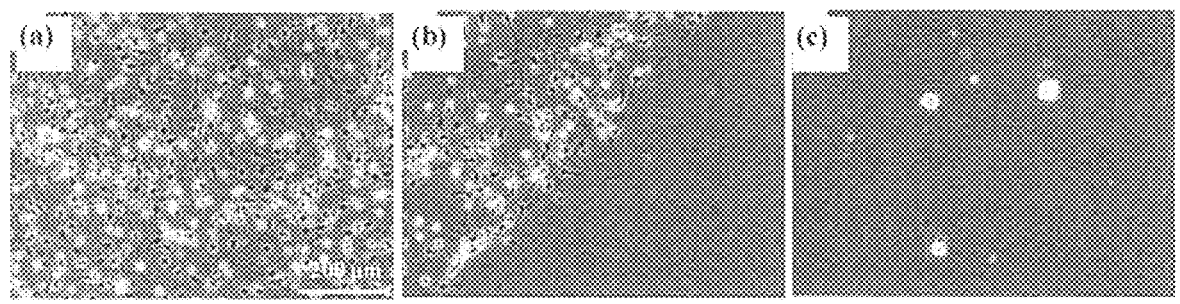
FIG. 7 is a set of microphotographs showing the state of cell adhesion after a 3-day cell culture on the cell culture substrate of Example 1 that had been irradiated with ultraviolet light (360-370 nm) in a particular area of it. The left column shows the irradiated area, the right column the unirradiated area, and the middle column an intermediate area between the two. The bar in a photograph corresponds to 200 μm.

(b) Evaluation of Surface Modification by Excitation Light (360-370 nm) from Fluorescence Microscope Evaluation was conducted of cell-adhesibleness to the PMEGAm brush-constructed surface that had been irradiated with the excitation light from the florescence macroscope for 30 minutes. FIG. 6 shows microphotographs of the PMEGAm surface after a one-day cell culture, and FIG. 7 that of a three-day culture. In FIG. 6 and FIG. 7, (a), (a)', and (a)" show microphotographs of the irradiated area; (b), (b)', and (b)" of border area between the irradiated and the unirradiated areas, (c), (c)', and (c)" of the unirradiated area.

As seen where UV irradiation (300-400 nm) was carried out using the UV irradiator, no cell adhesion or spreading of adhering cells was observed on the PMEGAm brush-constructed surface of the unirradiated areas (FIGS. 6(c), 7(c), etc.). Cell adhesion, and spreading of adhering cells were observed in the irradiated areas (FIGS. 6(a), 7(a), etc.). The results demonstrate that it is also possible to modify the PMEGAm brush-constructed surface and to realize position-specific adhesion of cells, by irradiation with the excitation light having a wavelength of 360-370 nm.

(Example 2) Modification of Substrate Surface with P(MEGAm-r-MPTMS)

[Chem. 13]

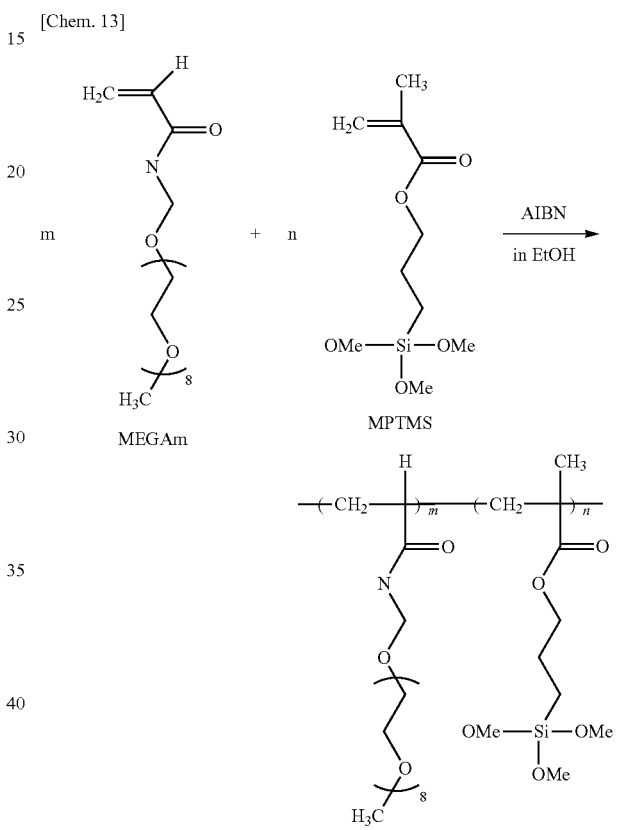

1. Synthesis of poly(MEGAm-r-MPTMS)

Copolymerization of MEGAm and trimethylsilylpropylmethacrylate (MPTMS) were performed in ethanol using AIBN as polymerization initiator, varying the blending ratio of monomers and initiator, respectively, as shown in Table 2 below, three different type of poly(MEGAm-r-MPTMS), each having high molecular weight and low molecular weight.

TABLE 2

Conditions in synthesis of P(MEGAm-r-MPTMS)

| High molecular weight polymer | HMW(85:15) | HMW(90:10) | HMW(95:5) |
|---|---|---|---|
| MEGAm | 3.18 mL | 3.36 mL | 3.55 mL |
| MPTMS | 0.3953 mL | 0.2636 mL | 0.1318 mL |
| AIBN | 0.00304 g | 0.00304 g | 0.00304 g |
| Dry ethanol | 10 mL | 10 mL | 10 mL |
| Molar input ratio | 510:90:1 | 540:60:1 | 570:30:1 |

TABLE 2-continued

Conditions in synthesis of P(MEGAm-r-MPTMS)

| Low molecular weight polymer | LMW(85:15) | LMW(90:10) | LMW(95:5) |
|---|---|---|---|
| MEGAm | 3.18 mL | 3.36 mL | 3.55 mL |
| MPTMS | 0.3953 mL | 0.2636 mL | 0.1318 mL |
| AIBN (1st) | 0.0912 g | 0.0912 g | 0.0912 g |
| AIBN (2nd) | 0.0182 g | 0.0182 g | 0.0182 g |
| Dry ethanol | 10 mL | 10 mL | 10 mL |
| Molar input ratio | 14.2:2.5:1 | 15:1.7:1 | 15.9:0.8:1 |

2. Modification of Substrate Surface

Each of the above six different poly(MEGAm-r-MPTMS) was prepared into a 10 mg/mL ethanol solution, in which a glass substrate plate that had been washed was immersed and reaction was allowed to proceed for 12 hours at 50° C. After the reaction, the plate was washed with methanol and water, dried, and its surface was modified as schematically shown below to provide a cell culture substrate.

[Chem. 14]

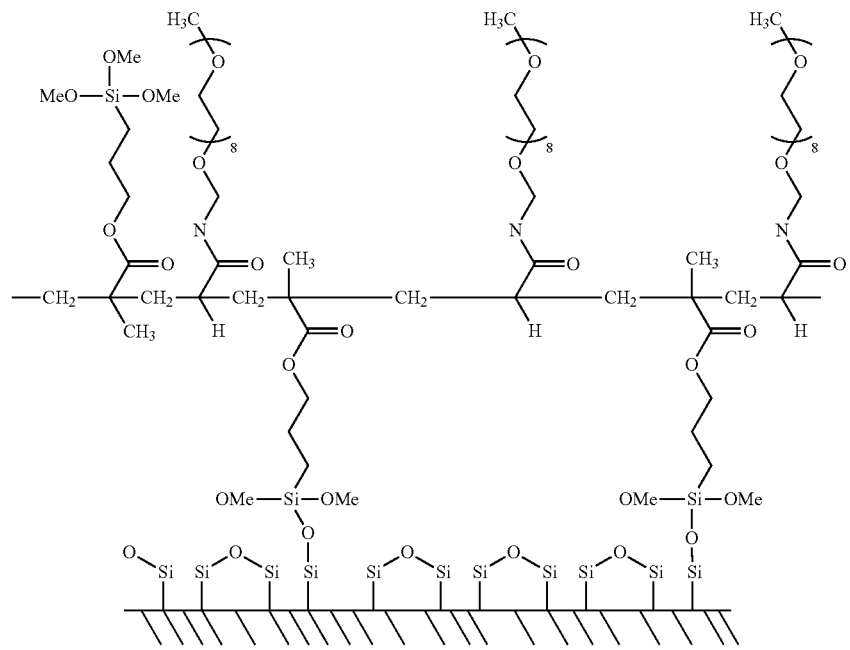

3. UV Modification of the Surface of Cell Culture Substrate

Each of different substrate plates prepared above was irradiated in a dry state with ultraviolet light having a wavelength of 360-370 nm (irradiation intensity: 97 mW/cm$^2$) for 100 minutes, then washed with water and methanol, and sterilized by immersing in 70% ethanol and air drying in a clean bench. The plate was immersed in a culture medium containing serum ingredients, and left undisturbed until seeding of cells.

4. Change in Contact Angle of Poly(MEGAm-r-MPTMS)-Modified Surface by Ultraviolet Irradiation The contact angle to the surface of each of the six different substrate plates modified above with poly(MEGAm-r-MPTMS) was measured in its ultraviolet light (360-370 nm)-irradiated area and unirradiated area, and compared, as done in Example 1. The results are shown in the following table and FIG. 8.

TABLE 3

| Contact angle to poly(MEGAm-r-MPTMS)-modified surface | | |
|---|---|---|
| Samples | UV unirradiated (°) | UV irradiated (°) |
| HMW(85:15) | 46.8 (±1.4) | 49.4 (±3.3) |
| HMW(90:10) | 42.7 (±1.2) | 47.9 (±1.9) |
| HMW(95:5) | 41.0 (±1.9) | 44.3 (±2.7) |
| LMW(85:15) | 46.2 (±1.5) | 50.5 (±1.4) |
| LMW(90:10) | 42.8 (±1.6) | 46.0 (±2.1) |
| LMW(95:5) | 40.7 (±1.2) | 42.9 (±3.2) |

Figure 8:
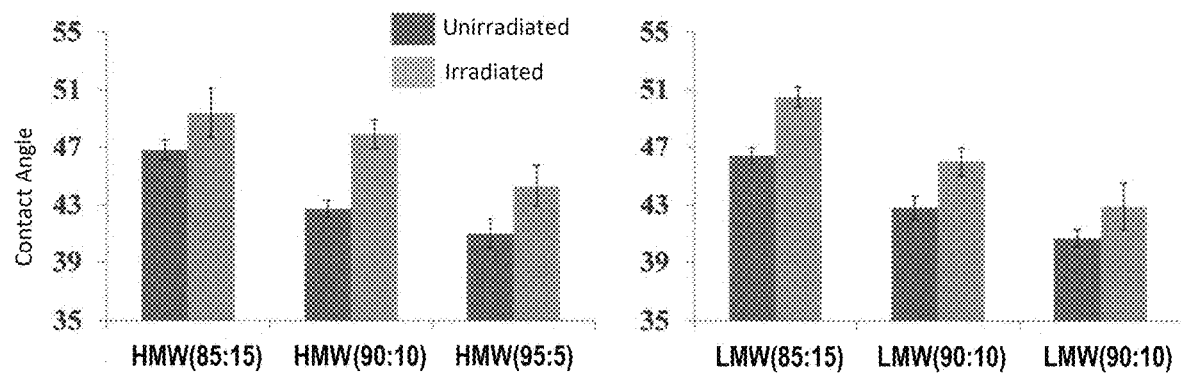
FIG. 8 is a set of graphs illustrating the difference in contact angle between the irradiated and the unirradiated areas of the cell culture substrate of Example 2 that had been irradiated with ultraviolet light (360-370 nm) in a particular area of it.

As seen in Table 3 and FIG. 8, it was confirmed that contact angle increased by ultraviolet light irradiation in any of the polymers.

5. Change in the Amount of Protein Adsorbed by Poly (MEGAm-r-MPTMS)-Modified Surface The difference in the amount of adsorbed proteins by each of the substrate surface that had been modified with the six different poly(MEGAm-r-MPTMS) before and after irradiation with ultraviolet light (360-370 nm).

Namely, in the same manner as the above, each of the substrate plates, before and after irradiated with ultraviolet light (360-370 nm), was immersed in a phosphate buffer solution containing dissolved serum albumin (20 mg/mL), left undisturbed for two hours at room temperature, and then loosely adsorbed proteins were removed by washing with a phosphate buffer. Each of those substrate plates was immersed in a bicinchoninic acid protein measurement solution and allowed to react for 2 hours at 37° C., and the coloration of the solution was measured on an ultraviolet visible spectrophotometer (measurement wavelength: 570 nm) to determine and compare the amount of proteins adsorbed by the substrate surface (ng/cm$^2$). The results are shown in Table 4 and FIG. 9.

TABLE 4

Protein adsorption by poly(MEGAm-r-MPTMS)-modified surface

| Samples | UV unirradiated (°) | UV irradiated (°) |
|---|---|---|
| HMW(85:15) | 37.5 (±34.9) | 103 (±43.3) |
| HMW(90:10) | 55.9 (±31.5) | 182 (±53.5) |
| HMW(95:5) | 46.6 (±43.4) | 103 (±40.8) |
| LMW(85:15) | 64.0 (±38.3) | 129 (±35.3) |
| LMW(90:10) | 19.0 (±17.7) | 214 (±82.0) |
| LMW(95:5) | 37.2 (±27.3) | 87.1 (±36.2) |

Figure 9:
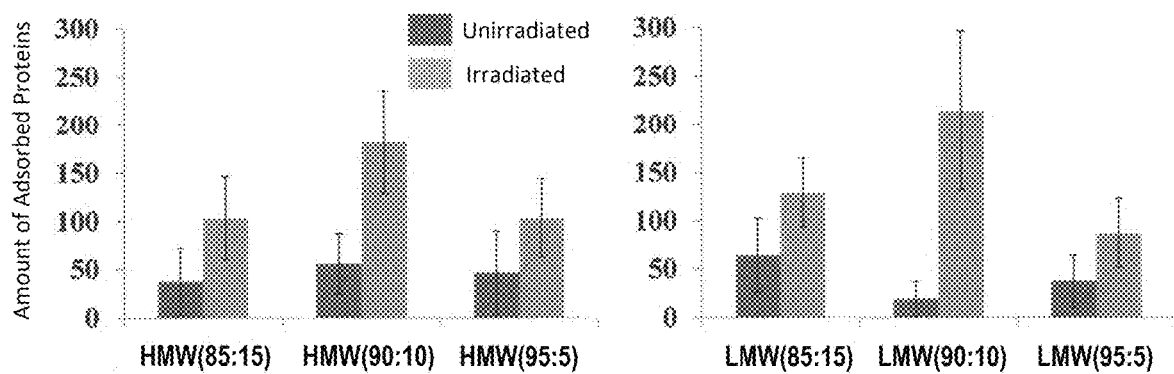
FIG. 9 is a set of graphs illustrating the difference in protein adhesion between the irradiated and the unirradiated areas of the cell culture substrate of Example 2 that had been irradiated with ultraviolet light (360-370 nm) in a particular area of it.

As evident from Table 4 and FIG. 9, irradiation with ultraviolet light markedly increased the amount of adsorbed proteins with all the polymers.

6. Change in Cell Adhesibleness by UV Irradiation of Poly(MEGAm-r-MPTMS)-Modified Surface Each of the six kinds of surface-modified substrate plates was irradiated with ultraviolet light (360-370 nm) in the same manner as above, and used to culture cells as in Example 1 to compare cell adhesibleness between the ultraviolet light-irradiated and unirradiated areas.

Figure 10:
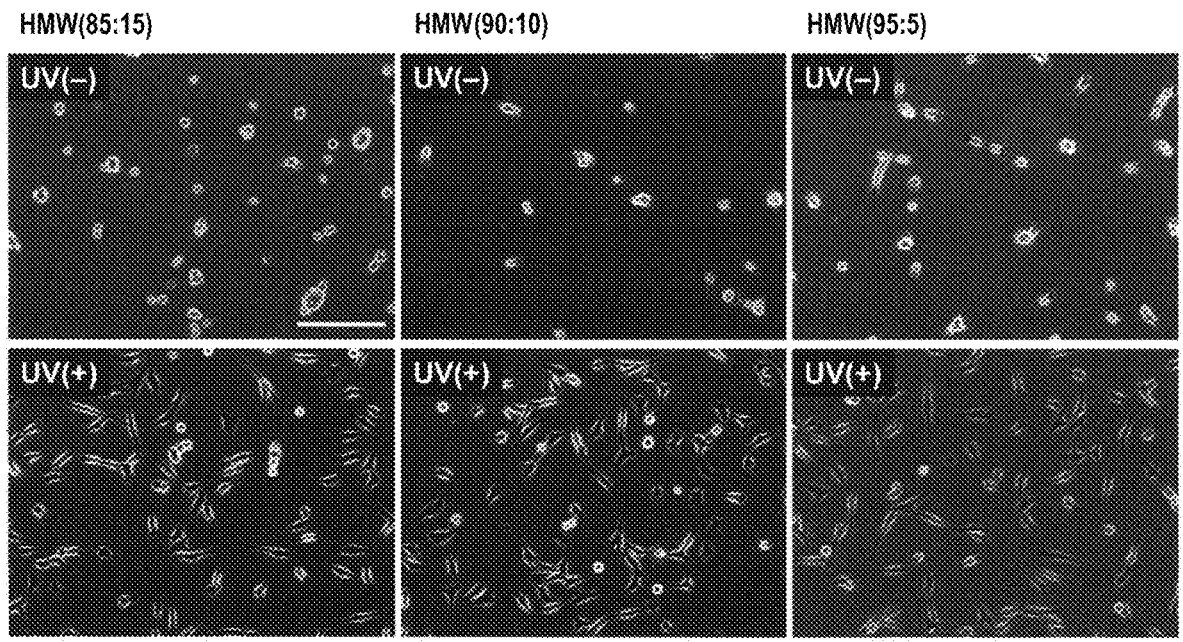
FIG. 10 is a set of microphotographs showing the state of cell adhesion after a one-day cell culture on the cell culture substrate of Example 2 (high molecular weight type) that had been irradiated with ultraviolet light (360-370 nm) in a particular area of it. The upper stage corresponds to the ultraviolet light unirradiated area (UV(−)), and the lower stage to the ultraviolet light irradiated area (UV(+)). The bar in a photograph corresponds to 200 μm, and the magnification ratios of all the photographs are the same.
Figure 11:
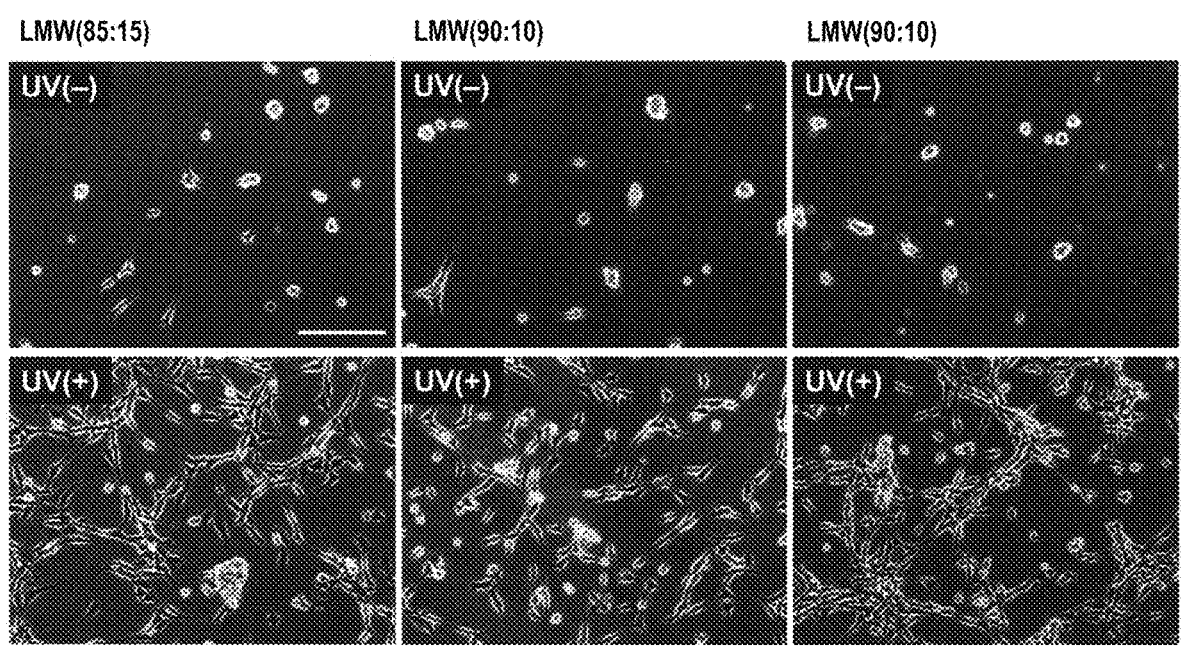
FIG. 11 is a set of microphotographs showing the state of cell adhesion after a 3-day cell culture on the cell culture substrate of Example 2 (low molecular weight type) that had been irradiated with ultraviolet light (360-370 nm) in a particular area of it. The upper stage corresponds to the ultraviolet light unirradiated areas (UV(−)), and the lower stage to the ultraviolet light irradiated areas (UV(+)). The bar in a photograph corresponds to 200 μm, and the magnification ratio is the same in all the photographs.

As a result, cell adhesion was remarkable in the ultraviolet light-irradiated area with every surface-modified substrate plate, and no or very little adhesion was observed in the unirradiated area. And while the cells in the irradiated area showed brisk spreading, that was rarely seen in the unirradiated area. Typical examples are shown in FIG. 10 in the high molecular weight three polymers, and in FIG. 11 in the low molecular weight three polymers, respectively, with microphotographs. In the figures, the upper stage corresponds to the ultraviolet light unirradiated areas (UV(−)), and the lower stage to the ultraviolet light irradiated areas (UV(+)).

INDUSTRIAL APPLICABILITY

The present invention is useful as its enables culturing cells in a state that they adhere exclusively to a particular area, and also culturing different kinds of cells in a state that they adhere to their particular areas, respectively, as well as realizes the same by a conventional and low-cost way.

REFERENCE SIGNS LIST

1 Glass
2 Polystyrene-petri dish for cell culture
3 Ultraviolet light
4 Lens

The invention claimed is:

1. A photomodifiable polymer comprising: as a component (A), a monomer represented by Formula (1):

$$\text{(Formula 1)}$$

wherein R1 denotes a hydrogen or a methyl group, and R2 denotes an alkyl group having 1-22 carbon atoms, and n denotes an integer of 1-30, the polyethylene glycol moiety in Formula (1) is cleavable by irradiation with an ultraviolet light having a wavelength from 300 nm to 400 nm; and a component (B) having a trialkoxysilyl group, wherein the molar ratio of the component (A) and the component (B), that is component (A):component (B), is in a range from 85:15 to 98:2, the photomodifiable polymer comprises a polymer chain comprising a polymerized component (A) and the trialkoxysilyl group of component (B) bonded to the end of the polymer chain, wherein the polymer chain has a structure represented by the Formula (3):

$$\text{(Formula 3)}$$

wherein R8 denotes an aromatic group that may have one or more saturated hydrocarbon groups having 1-4 carbon atoms; R9 denotes a hydrogen or a methyl group; each of R10, R11, and R12 independently denotes an alkoxyl group having 1-4 carbon atoms; Z denotes a group —S—C(S)—S—R13, wherein R13 denotes an alkyl group having 1-6 carbon atoms, and a group at a free end of is $CH_3$, and when the polyethylene glycol moiety of the component (A) is cleaved by the ultraviolet light, the photomodifiable polymer becomes receptive to cell adhesion.

2. A cell culture substrate comprising a base material and a polymer layer formed on the surface thereof, wherein the polymer layer consists of the photomodifiable polymer according to claim 1, and is held on the base material with a bond produced by a reaction between the trialkoxysilyl group of the component (B) and the base material.

3. The cell culture substrate according to claim 2, wherein the base material consists of glass, ceramic, metal, or of a resin treated with a glass-based primer.

4. A method for producing a cell culture substrate, wherein the method comprises applying the photomodifiable polymer according to claim 1 to a surface of a base material.

5. A method for producing a cell culture substrate, wherein the method comprises copolymerizing a component (A) and a component (B) on a base material, wherein the component (A) is a monomer represented by Formula (1):

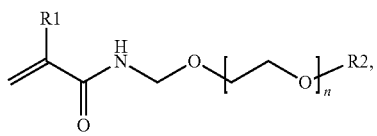

(1)

wherein R1 denotes a hydrogen or a methyl group, and R2 denotes an alkyl group having 1-22 carbon atoms, and n denotes an integer of 1-30, and the component (B) is a monomer having a trialkoxysilyl group, the molar ratio of the component (A) and the component (B), that is component (A):component (B), is in a range from 85:15 to 98:2, the photomodifiable polymer comprises a polymer chain comprising a polymerized component (A) and the trialkoxysilyl group of component (B) bonded to the end of the polymer chain, wherein the polymer chain has a structure represented by the Formula (3):

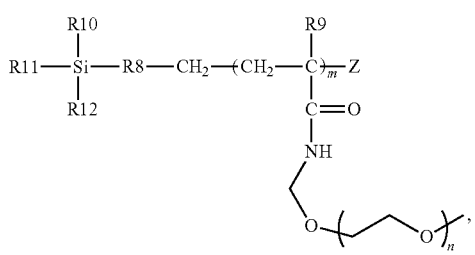

(3)

wherein R8 denotes an aromatic group that may have one or more saturated hydrocarbon groups having 1-4 carbon atoms; R9 denotes a hydrogen or a methyl group; each of R10, R11, and R12 independently denotes an alkoxyl group having 1-4 carbon atoms; Z denotes a group —S—C(S)—S—R13, wherein R13 denotes an alkyl group having 1-6 carbon atoms, and a group at a free end of

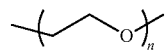

is $CH_3$, the polyethylene glycol moiety in Formula (1) is cleavable by irradiation with an ultraviolet light having a wavelength from 300 nm to 400 nm, and when the polyethylene glycol moiety of the component (A) is cleaved by the ultraviolet light, the photomodifiable polymer becomes receptive to cell adhesion.

6. The method according to claim 5, wherein the base material consists of glass, ceramic, metal, or of a resin treated with a glass-based primer.

7. A method for coculturing different kinds of cell populations in a state that they adhere to a same substrate in areas thereof that respectively correspond to the different kinds of the cell populations, comprising:

irradiating a first area of the cell culture substrate according to claim 2 with ultraviolet light to modify the first area, and then culturing a first kind of cells on the substrate to let the population of the first kind of cells adhere to the first area; and irradiating a second area of the substrate different from the first area with ultraviolet light to modify the second area, and then culturing a second kind of cells different from the first kind of cells on the substrate to let the population of the second kind of cells adhere to the second area.

\* \* \* \* \*